United States Patent
Pfaff et al.

(10) Patent No.: US 6,334,893 B1
(45) Date of Patent: Jan. 1, 2002

(54) PIGMENT MIXTURE

(75) Inventors: Gerhard Pfaff, Münster; Sabine Schoen, Darmstadt, both of (DE); Kaiman Shimizu, Fukushima-pref (JP)

(73) Assignee: Merck Patent Gesellschaft mit Beschrankter Haftung, Darmstadt (DE)

(*) Notice: Subject to any disclaimer, the term of this patent is extended or adjusted under 35 U.S.C. 154(b) by 0 days.

(21) Appl. No.: 09/471,004

(22) Filed: Dec. 23, 1999

(30) Foreign Application Priority Data

Dec. 23, 1998 (EP) .............................. 98124474

(51) Int. Cl.$^7$ .............................. C09C 1/00; C09D 11/02
(52) U.S. Cl. .................. 106/442; 106/410; 106/415; 106/436; 106/439; 106/445; 106/446; 106/453; 106/454; 106/456; 106/457; 106/459; 106/460; 106/474; 106/483; 106/493; 106/494; 106/495; 106/498
(58) Field of Search .................... 106/436, 439, 106/442, 445, 410, 415, 446, 453, 454, 456, 457, 459, 460, 474, 483, 493, 494, 495, 498

(56) References Cited

U.S. PATENT DOCUMENTS 5,702,519 A * 12/1997 Nitta et al. .................. 106/442
6,019,831 A * 1/2000 Schmidt et al. ............. 106/417

FOREIGN PATENT DOCUMENTS

| EP | 1 013 722 | * | 6/2000 |
| EP | 1 013 724 | * | 6/2000 |
| EP | 1 013 725 | * | 6/2000 |
| EP | 1 045 014 | * | 10/2000 |
| JP | 11-140346 | * | 5/1999 |
| JP | 2000-86945 | * | 3/2000 |

* cited by examiner

Primary Examiner—Anthony Green
(74) Attorney, Agent, or Firm—Millen, White, Zelano & Branigan, P.C.

(57) ABSTRACT

The present invention relates to pigment mixtures containing at least two components component A being $Al_2O_3$ flakes coated with one or more metals, metal oxides and/or metal sulfides and component B being acicular or spherical colorants, and to their use in particular in varnishes, paints, printing inks, powder coating materials, plastics and cosmetic formulations.

21 Claims, No Drawings

PIGMENT MIXTURE

SUMMARY OF THE INVENTION

The present invention relates to pigment mixtures containing at least two components, component A being $Al_2O_3$ flakes coated with one or more metals, metal oxides, and/or metal sulfides and component B being acicular or spherical colorants, and to their use in varnishes, paints, printing inks, plastics, powder coating materials and cosmetic formulations.

With platelet-shaped pigments, hiding power and gloss are often difficult to realize simultaneously to a satisfactory extent. For instance, $SiO_2$ flakes or mica platelets covered with one or more thin metal oxide layers feature interference colors and a high luster but at the same time, owing to the transparent substrate, feature high transparency and hence a comparatively poor hiding power.

DE-A-42 40 511 discloses a pigment mixture which is composed of an interference pigment and a platelet-shaped color pigment. The interference pigment comprises mica flakes or $SiO_2$ flakes coated with metal oxides and the color pigment can be colored, uncoated $SiO_2$ flakes. This pigment mixture is incorporated into coating materials, printing inks or plastics.

It is the object of the present invention to provide a pigment mixture which is notable for a comparatively high hiding power, which lends itself well to incorporation into the respective system in which it is used and for which at the same time the separation of pigment/colorant in the system is substantially ruled out.

Surprisingly, a pigment mixture has now been found which has none of the disadvantages indicated above. The pigment mixture of the invention consists of at least two components, component A being $Al_2O_3$ flakes coated with one or more metals, metal oxides and/or metal sulfides and component B being acicular or spherical colorants.

By admixing the colorant with the coated $Al_2O_3$ flakes it is possible to give the systems in which they are used a multiple flop, the color effect is intensified, and new color effects are achieved.

The invention thus provides a pigment mixture containing at least two components, component A and component B. Component A comprises $Al_2O_3$ flakes coated with one or more metals, metal oxides and/or metal sulfides. The $Al_2O_3$ flakes comprise platelet shaped $Al_2O_3$ substrates. Component B comprises acicular or spherical colorants.

The invention likewise provides the formulations, such as paints, varnishes, printing inks, plastics, powder coating materials and cosmetic formulations, which comprise the pigment mixture of the invention.

The coated $Al_2O_3$ flakes can be mixed with the colorant in any ratio. Preferably, the ratio of component A to component B is from 1:10 to 10:1, in particular from 1:2 to 2:1.

The most important constituent of the inventive pigment mixture is the $Al_2O_3$ flake. Aluminum oxide in a flaky form is commercial available for example from Merck KGaA under the tradename Xirallic®.

$\alpha$-$Al_2O_3$ in the form of hexagonal flakes having a particle diameter greater than 10 $\mu$m and an aspect ratio (particle diameter/thickness) of 5–10 is known from JP 111239/1982 (Laid Open No.).

The Japanese Patent Publication No. 72527/1991 discloses $\alpha$-$Al_2O_3$ in the form of flakes having an average particle diameter of 0.5–3 $\mu$m.

The JP 39362/1992 (Laid Open No.) describes $Al_2O_3$ in the form of fine platy particles of a hexagonal crystal system with the plane perpendicular to the c axis grown into a plate.

Preferred $Al_2O_3$ flakes are flakes composed of aluminum oxide (as a major constituent) and of titanium dioxide (as a minor constituent) which are known from U.S. Pat. No. 5,702,519. These $Al_2O_3$ flakes are prepared from a uniform aqueous solution of water-soluble aluminum salt and titanium salt by hydrolysis with an alkali carbonate aqueous solution in the presence of an aqueous solution containing an alkali metal salt like alkali metal sulfate and phosphoric acid or phosphate, drying by evaporation (dehydration by heating), and molten salt treatment.

The $Al_2O_3$ flakes are provided with one or more metal oxide layers. Examples of suitable metal oxides or metal oxide mixtures are titanium dioxide, zirconium oxide, zinc oxide, iron oxides ($Fe_2O_3$ and/or $Fe_3O_4$) and/or chromium oxide, especially $TiO_2$ and/or $Fe_2O_3$, as described in U.S. Pat. No. 5,702,519.

Coating of the $Al_2O_3$ flakes with a metal oxide may be accomplished by any known methods, such as hydrolysis of a metal salt by heating, or alkali, which deposits hydrated metal oxide, followed by calcination.

$Al_2O_3$ flakes can also be coated with one or more layers of a metal or metal alloys selected from, for example, chromium, nickel, bismuth, copper, tin or hastalloy.

$Al_2O_3$ flakes coated with a metal sulfide are coated with, for example, sulfides of tungsten, molybdenum, cerium, lanthanum or rare earth elements.

The $Al_2O_3$ flakes can be coated by wet chemical coating, by CVD or PVD processes. The metal coating on the $Al_2O_3$ flakes functions to increase the hiding power of the pigment.

Colorants suitable as component B for the pigment mixture of the invention are all acicular and spherical colorants which are known to the skilled worker and have a particle size of from 0.001 to 20 $\mu$m, preferably from 0.01 to 3 $\mu$m. By acicular, fiber-like particles are meant those having a length-to-diameter ratio of more than 5. Spherical colorants are here defined not only as ideal shaped spheres but also for particles which have more or less spherical shape of a non-uniform diameter. The pigment mixtures of the invention preferably comprise, as colorants, absorption materials and fillers.

The spherical colorants include, in particular, $TiO_2$, colored $SiO_2$, $CaSO_4$, iron oxides, chromium oxides, carbon black, organic color pigments, such as anthraquinone, quinacridone, diketopyrrolopyrrole, phthalocyanine, azo and isoindoline pigments. The acicular pigments preferably comprise BiOCl, colored glass fibers, $\alpha$-$Fe_2O_3$, $\alpha$-FeOOH organic color pigments, such as azo pigments, $\beta$-phthalocyanine CI Blue 15.3, Cromioplhtal Yellow 8GN (Ciba-Geigy), Irgalith Blue PD56 (Ciba-Geigy), azomethine copper complex CI Yellow 129, Irgazine Yellow 5GT (Ciba-Geigy).

The pigment mixture of the invention is simple and easy to handle. The pigment mixture can be incorporated into the system in which it is used simply by stirring it in. Laborious milling and dispersing of the pigments is not necessary.

The pigment mixture of the invention can be used for pigmenting coating materials, printing inks, plastics, agricultural films, the coating of seeds, food colorings, button pastes, medicament coatings or cosmetic formulations. The concentration of the pigment mixture in the system in which it is to be used for pigmenting is generally between 0.1 and 70% by weight, preferably between 0.1 and 50% by weight and, in particular, between 1.0 and 10% by weight, based on the overall solids content of the system. It is generally dependent on the specific application.

The pigment mixtures of the invention may also be used for food enhancement. Food enhancements may include, for example, coating no foods such as cakes and sweets to give them an interesting luster effect. Food enhancements may also include the incorporation of the pigment mixture into foods such as, for example, chewing gums and pudding.

Plastics comprising the pigment mixture of the invention in amounts of 0.01 to 50% by weight, in particular from 0.1 to 7% by weight, are frequently notable for a particular sparkle effect.

In the coating sector, especially in automotive finishing, the pigment mixture is employed—for 3-coat systems as well—in amounts of 0.1–10% by weight, preferably from 1 to 3% by weight. The proportion in which the coated $Al_2O_3$ flakes are mixed with component B depends on the desired effect. The $Al_2O_3$ flakes are preferably employed with component B in a proportion of 1:10 to 1:1, in particular of 1:3.

In the coating material, the pigment mixture of the invention has the advantage that certain color flop effects can be achieved by a single-layer coating (one-coat system or basecoat in a two-coat system). This color flop is pronounced even under diffuse light. In comparison with coating systems which comprise a mica-based interference pigment rather than the coated $Al_2O_3$ flakes, coating systems with the pigment mixture of the invention exhibit a more marked depth effect and a glitter effect.

The pigment mixture of the invention can also be employed in decorative and grooming cosmetology. The use concentration and the mixing proportion of $Al_2O_3$ flakes with component B, especially organic and inorganic color pigments and dyes, of natural or synthetic origin, such as chromium oxide, ultramarine, or spherical $SiO_2$ or $TiO_2$ pigments, are dependent on the medium in which they are used and on the effect that is to be achieved. The $Al_2O_3$ flakes can be mixed with other pigments in any proportions, the preferred ratio being from 1:10 to 10:1. The use concentration ranges from 0.01% by weight in a shampoo to 70% by weight in a compact powder. In the case of a mixture of $Al_2O_3$ flakes with spherical fillers, such as $SiO_2$, the concentration in the formulation can be 0.01–70% by weight. The cosmetic products, such as nail varnishes, lipsticks, compact powders, shampoos, loose powders and gels, are notable for particularly interesting luster effects and/or color effects. The glitter effect in nail varnish can be increased markedly relative to conventional nail varnishes with the aid of the pigment mixtures of the invention. Furthermore, the pigment mixture of the invention can be employed in bath products, in tooth pastes and for enhancing foods, for example as a mass colorant or as a coating.

In the pigmentation of binder systems, for example, paints and printing inks for intaglio, offset printing or screen printing, or as a precursor for printing inks, in the form for example of highly pigmented pastes, granules, pellets, etc., pigment mixtures, especially those consisting of coated $Al_2O_3$ flakes and spherical colorants, such as $TiO_2$, carbon black, chromium oxide, iron oxide and also organic absorption pigments, have been found particularly suitable. The pigment mixture is generally incorporated into the printing ink in amounts of 2–35% by weight, preferably 5–25% by weight and, in particular, 8–20% by weight. Offset printing inks may comprise the pigment mixture in an amount of up to 40% by weight or more. The precursors of printing inks, in the form for example of granules, pellets, briquettes, etc., contain up to 95% by weight of the pigment mixture of the invention in addition to the binder and additives. The mixing ratio of component A to component B is preferably in the range from 1:10 to 10:1. The printing inks comprising the pigment mixture of the invention exhibit purer hues and their printability is improved owing to the good viscosity values.

The invention hence also provides formulations containing the pigment mixture of the invention.

In the foregoing and in the following examples, all temperatures are set forth uncorrected in degrees Celsius; and, unless otherwise indicated, all parts and percentages are by weight.

The entire disclosure of all applications, patents and publications, cited herein are hereby incorporated by reference. Particularly, this application claims priority to European Patent Application 98124474.2, the entire text of which is hereby incorporated by reference. Additionally, U.S. patent application Ser. Nos. 09/471,331, 09/471,269, and Ser. No. 09/471,330 are hereby incorporated by reference.

EXAMPLES

Example 1

Printing Ink

The pigment was incorporated into the solvent-containing binder by stirring at 600 rpm and the printing inks were subsequently knife-coated onto black-and-white cards.

Ink No. 1:

88.0 g Gebr. Schmidt 95 MB 011 TW 10.0 g $Fe_2O_3$-coated $Al_2O_3$ flakes of particle size 5 to 60 μm 2.0 g Gebr. Schmidt 95 MB 022-TW (Green)

Ink No. 2: Comparison 88.0 g Gebr. Schmidt 95 MB 011 TW 10.0 g $Fe_2O_3$-coated mica of particle size 10 to 60 μm 2.0 g Gebr. Schmidt 95 MB 022-TW (Green)

The color card with ink No. 1 exhibits in visual terms a markedly better depth and glitter effect than the color cards with the comparison ink No. 2.

Example 2

Automotive Finish 2.0 g $Fe_2O_3$-coated $Al_2O_3$ flakes of particle size 5–60 μm 1.5 g Heliogen Blue L 6930

0.2 g Hostaperm Green 8G 0.05 pigment-grade carbon black FW 200

66.6 g basecoat (A4) MP system (FK=19%)

29.65 g diluent mixture

Example 3

Plastic

Granules of the plastics polypropylene PP Stamylan PPH10 (from DSM) and polystyrene 143E (from BASF) are admixed in each case with a) 1% of $Fe_2O_3$-coated $Al_2O_3$ flakes of particle size 5–60 μm b) a mixture of 1% of $Fe_2O_3$-coated $Al_2O_3$ flakes of particle size 5–60 μm and 0.1% of PV Fast Blue B2G01 (Pigment Blue 15.3 from Clariant)

c) 1% of $Fe_2O_3$-coated mica of particle size 10–60 μm d) a mixture of 1% of $Fe_2O_3$-coated mica of particle size 10–60 μm and 0.1% of PV Fast Blue B2G01 (Pigment Blue 15.3 from Clariant).

The pigmented granules are subsequently processed on an injection moulding machine to form small stepped plates. The plates differ in their color flops.

Example 4
Eye Shadow

| Phase A | |
|---|---|
| 5.00% | Silica |
| 25.00% | TiO$_2$-coated Al$_2$O$_3$ flakes of particle size 5–60 μm (from Merck KGaA) |
| 5.00% | CI Pigment Green 18 (CI77289) |
| 47.42% | Talc |
| 7.18% | Solanum Tuberosum (potato starch) |
| 2.40% | Magnesium stearate |
| Phase B | |
| 6.96% | Isopropyl stearate |
| 0.40% | Cetyl palmitate |
| 0.40% | Petrolatum |
| 0.08% | Preservative |

The constituents of phase A are combined and formed into a premix. The melted phase B is then added dropwise with stirring to the powder mixture. The powders are pressed at 40–50 bar.

Example 5
Lipstick

| Phase A | |
|---|---|
| 8.25% | Cera alba |
| 4.95% | Ceresin, Copernica Cerifera |
| 3.30% | Lanolin oil |
| 5.28% | Isopropyl myristate |
| 1.98% | Mineral oil |
| 0.03% | Tocopherol, ascorbyl palmitate, ascorbic acid, citric acid, PEG-8 |
| 0.06% | Preservative |
| 0.50% | Aroma |
| 1.00% | Lithol rubine BK, C.I. Pigment Red 57:1 (C1 15850) |
| ad 100.00% | Ricinus Communis (20% in castor oil) |
| Phase B | |
| 2.00% | Silica |
| 15.00% | Iron oxide-coated Al$_2$O$_3$ flakes of particle size 5–60 μm (from Merck KGaA) |

The constituents of phase A are heated to 75° C. and melted. The pigments of phase B are added and the entire batch is stirred thoroughly. The lipstick composition is then stirred for 15 minutes in the casting apparatus which has been preheated to 65° C. The homogeneous melt is poured into the casting molds, which have been preheated to 65° C. The molds are then cooled and the cold moldings removed.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A pigment mixture comprising a component A and a component B, wherein component A comprises Al$_2$O$_3$ flakes coated with one or more metals, metal oxides and/or metal sulfides, and wherein component B comprises at least one acicular colorant or at least one spherical colorant.

2. A pigment mixture according to claim 1, wherein component A comprises Al$_2$O$_3$ flakes having a coating comprising TiO$_2$, Fe$_2$O$_3$, or a mixture of TiO$_2$ and Fe$_2$O$_3$.

3. A pigment mixture according to claim 1, wherein component B comprises at least one of colored glass particles, carbon black, organic color pigments or inorganic color pigments.

4. A pigment mixture according to claim 2, wherein component B comprises at least one of colored glass particles, carbon black, organic color pigments or inorganic color pigments.

5. A pigment mixture according to claim 1, wherein component A and component B are mixed in a ratio of from 10:1 to 1:10.

6. A pigment mixture according to claim 2, wherein Component A and component B are mixed in a ratio of from 10:1 to 1:10.

7. A pigment mixture according to claim 3, wherein component A and component B are mixed in a ratio of from 10:1 to 1:10.

8. A pigment mixture according to claim 4, wherein Component A and component B are mixed in a ratio of from 10:1 to 1:10.

9. A pigment mixture according to claim 1, wherein the acicular colorant or spherical colorant has a particle size of from 0.001 to 20 μm.

10. A pigment mixture according to claim 2, wherein the acicular colorant or the spherical colorant has a particle size of from 0.0 01 to 20 μm.

11. A pigment mixture according to claim 1, wherein the acicular colorant or the spherical colorant has a particle size of from 0.01 to 3 μm.

12. A pigment mixture according to claim 2, wherein the acicular colorant or the spherical colorant has a particle size of from 0.01 to 3 μm.

13. A pigment mixture according to claim 1, wherein component B is TiO$_2$, colored SiO$_2$, CaSO$_4$, iron oxides, chromium oxides, carbon black, anthraquinone, quinacridone, diketopyrrolopyrrole, phthalocyanine, azo or isoindoline pigmemts, BiOCl, colored glass fibers, or α-Fe$_2$O$_3$ or α-FeOOH organic color pigments.

14. A method of manufacturing a pigment formulation comprising providing a pigment mixture according to claim 1 and adding the pigment mixture to a formulation to obtain a varnish, a paint, an automotive finish, a printing ink, a plastic, a powder coating material, a formulation for coloring seed, a cosmetic formulation, or a formulation for food enhancement.

15. A method of manufacturing a pigment formulation comprising providing a pigment mixture according to claim 2 and adding the pigment mixture to a formulation to obtain a varnish, a paint, an automotive finish, a printing ink, a plastic, a powder coating material, a formulation for coloring seed, a cosmetic formulation, or a formulation for food enhancement.

16. A pigment formulation comprising a pigment mixture according to claim 1, wherein the pigment formulation is a varnish, a paint, an automotive finish, a printing ink, a plastic, a powder coating material, a formulation for coloring seed, a cosmetic formulation, or a formulation for food enhancement.

17. A pigment formulation comprising a pigment mixture according to claim 2, wherein the pigment formulation is a varnish, a paint, an automotive finish, a printing ink, a plastic, a powder coating material, a formulation for coloring seed, a cosmetic formulation, or a formulation for food enhancement.

18. A pigment formulation comprising a pigment mixture according to claim 2, wherein the pigment formulation is a varnish, a paint, an automotive finish, a printing ink, a plastic, a powder coating material, a formulation for coloring seed, a cosmetic formulation, or a formulation for food enhancement.

19. A pigment formulation according to claim 17, wherein the pigment formulation is a plastic and comprises 0.1% to 7% by weight of the pigment mixture.

20. A pigment formulation according to claim 17, wherein the pigment formulation is a printing ink and comprises 2% to 35% by weight of the pigment mixture.

21. A pigment formulation according to claim 17, wherein the pigment formulation is an automotive finish and comprises 1% to 3% by weight of the pigment mixture.

* * * * *